United States Patent
Alberti et al.

[11] Patent Number: 5,290,746
[45] Date of Patent: * Mar. 1, 1994

[54] TETRAVALENT METAL DIPHOSPHONATE-PHOSPHITE COMPOSITION IN MICROPOROUS SOLID CRYSTALLINE FORM, WITH A NARROW MICROPORE DISTRIBUTION

[75] Inventors: Giulio Alberti; Umberto Costantino, both of Perugia; Riccardo Vivani, Della Pieve-Perugia; Piergiorgio Zappelli; Antonio Rossodivita, both of Monterotondo-Rome, all of Italy

[73] Assignee: Eniricerche S.p.A., Milan, Italy

[*] Notice: The portion of the term of this patent subsequent to Nov. 24, 2009 has been disclaimed.

[21] Appl. No.: 809,587

[22] Filed: Dec. 17, 1991

[30] Foreign Application Priority Data

Dec. 21, 1990 [IT] Italy ................. 22484 A/90

[51] Int. Cl.$^5$ ............................... C07F 7/00
[52] U.S. Cl. ........................ 502/162; 556/13; 556/19; 556/51; 556/54
[58] Field of Search ............ 556/19, 13, 54; 502/162

[56] References Cited

U.S. PATENT DOCUMENTS

| | | | |
|---|---|---|---|
| 4,390,690 | 6/1983 | DiGiacomo et al. | 556/19 |
| 4,487,922 | 12/1984 | Dines et al. | 556/19 |
| 5,166,380 | 11/1992 | Alberti et al. | 556/19 |

FOREIGN PATENT DOCUMENTS 0010366 4/1980 European Pat. Off.

OTHER PUBLICATIONS

CA:106:183165g; 66–Surface Chem., Colloids, vol. 106, 1987.

Primary Examiner—Asok Pal
Attorney, Agent, or Firm—Hedman, Gibson & Costigan

[57] ABSTRACT

A tetravalent metal diphosphonate-phosphite composition definable by the following general formula:

$$M(O_3P-R-PO_3)_{1-x}(HPO_3)_{2x} \quad (I)$$

is described where:
M is a tetravalent metal;
x varies from 0.5 to 0.66;
R is an organic radical of bivalent aromatic type, carrying side groups which increase its steric hindrance.

The composition is in the form of a crystalline solid with a type α layered structure with the diphosphonic groups positioned to join said layers together by a covalent bond (pillared compounds). It has a B.E.T. surface area from 300 to 500 m$^2$/g depending on the nature of R in formula (I), and a porosity in the micropore radius range of less than 20 Å (Angstrom), such micropores contributing to the extent of more than 95% of the total area for the most crystalline materials.

16 Claims, 15 Drawing Sheets

● = PH GROUP OF PHOSPHITE
○ = OXYGEN
• = HYDROGEN

- ⊙ = PH GROUP OF PHOSPHITE
- ○ = OXYGEN
- • = HYDROGEN

TETRAVALENT METAL DIPHOSPHONATE-PHOSPHITE COMPOSITION IN MICROPOROUS SOLID CRYSTALLINE FORM, WITH A NARROW MICROPORE DISTRIBUTION

This invention relates to a tetravalent metal diphosphonate-phosphite composition in microporous solid crystalline form with a narrow micropore distribution, its production process and its uses.

G. Alberti, S. Allulli, U. Costantino and N. Tomassini in J. Inorg. Nucl. Chem., 40, 1113 (1978) describe the production of lamellar compounds with a structure similar to that of α-zirconium phosphate [α-Zr(HPO$_4$)$_2$.H$_2$O] by reacting phosphonic acids with tetravalent metal salts. These lamellar phosphonates can be represented by the general formula M(RPO$_3$)$_2$, where M is a tetravalent metal and R is an organic radical. A specific example is zirconium benzene phosphonate, the structure of which is shown in FIG. 1.

After this basic discovery, intensive research was undergone in this field because of the considerable application potential of the compounds obtained, with regard to which the following technical and patent literature can be cited: G. Alberti, U. Costantino and M. L. Luciani, J. Chromatog., 180, 45 (1979); G. Alberti and U. Costantino, J. Mol. Catal., 27, 235 (1984); G. Alberti, U. Costantino, J. Korney and M. L. Luciani, Reactive Polymers 4, 1 (1985); G. Alberti, U. Costantino and G. Perego, J. Solid State Chem., 63, 455 (1986); EP 10,366; EP 10,857; M. B. Dines and P. M. Di Giacomo, inorg. Chem. 20, 92 (1981); P. M. Di Giacomo and M. B. Dines, polyhedron, 1, 61 (1982); M. B. Dines, P. M. Di Giacomo, K. P. Coollahan, P. C. Griffith, R. H. Lane and R. E. Cooksey, A.C.S. Series 192, Cap. 13, ACS Washington D.C., 1982; M. B. Dines, R. E. Cooksey, P. C. Griffith and R. H. Lane, Inorg. Chem. 22, 1003 (1983); M. B. Dines and P. C. Griffith, Polyhedron 2, 607 (1983); C. Y. Ortiz-Avila and A. Clearfield, Inorg. Chem. 24, 1773 (1985); A. Clearfield, Design of New Materials, Plenum Press, New York (1987), pp. 121-134; and A. Clearfield, Chem. Rev. 88, 125 (1988).

EP 10,366 and EP 10,857 describe some compositions of the pillared type, prepared by reacting tetravalent metal salts with diphosphonic acids, of formula MR(PO$_3$)$_2$ (where M is a tetravalent metal and R is a bivalent organic radical), the structure of which is shown schematically in FIG. 2. Unfortunately because of the α structure of the layers, the distance between the central axes of adjacent pillars is only 5.3 Å. Taking account of the fact that the mean Van der Waals diameter is about 4.4 Å for pillars consisting of aliphatic chains and about 3.7 Å for pillars consisting of aromatic rings, it can be deduced that the free space between pillars is smaller than the diameter of the molecules and that the compositions obtained are therefore not useful as molecular sieves. To introduce a certain microporosity between the layers it has been proposed to dilute the pillars by partially replacing them with very small groups of R'-PO$_3$ type, such as H-PO$_3$, HO-PO$_3$ and CH$_3$-PO$_3$ (see for example Clearfield, already cited). The formation of microcavities in an idealized zirconium diphosphonate in which phosphite groups are present is shown schematically in FIG. 3. In this model the cavity dimensions depend essentially on the length of the R(PO$_3$)$_2$ pillar and the spacing between the pillars.

However in the known art the problem of obtaining a composition having not only high porosity in the interlayer region but also a narrow pore diameter distribution has not yet been solved. In particular the applicants have conducted certain studies on diphosphonic acid/phosphorous acid/zirconium salt systems (experimental examples 1, 2 and 3), with conclusions similar to those of the aforesaid Clearfield, ie that the molar fraction of R(PO$_3$)$_2$ groups replaceable by H-PO$_3$ groups becomes increasingly smaller as the degree of crystallinity increases, in that there is a strong tendency towards the segregation of two phases, one consisting of Zr(HPO$_3$)$_2$ and the other consisting of zirconium diphosphonate containing only a few phosphite groups. For example, it has been found experimentally that while in the case of zirconium diphosphonates of low degree of crystallinity it is not difficult to obtain substitutions up to 30-35% of R(PO$_3$)$_2$ groups (see experimental example 1), this percentage reduces drastically to only 5-15% in compositions having a high degree of crystallinity (see experimental example 2). Consequently using the phosphonic acids reported up to the present time in the literature, it is possible to obtain an appreciable microporosity due to the spacing created in the interlayer region by small HPO$_3$ groups only when the pillared compositions are prepared with a low degree of crystallinity. However in these circumstances, as is to be expected given the irregularity of the substituents, and as found by the aforesaid Clearfield, it is not possible to obtain a narrow micropore distribution in the interlayer region, this being a very important condition for the use of these compositions as molecular sieves and/or as catalysts for shape-selective catalysis.

The co-pending U.S. patent application Ser. No. 738 891 filed by the present applicant on Aug. 1, 1991 now U.S. Pat. No. 5,166,380, states that the presence of phosphorous in the synthesis of tetravalent metal diphosphonates in addition to creating a certain quantity of micropores in the interlayer region also induces the formation of mesopores, the quantity of which increases as the degree of the obtained materials decreases. From this it is apparent that by using those diphosphonic acids already reported in the literature for this synthesis in mixture with phosphorous acid, the following contrasting results are obtained:

if operating in such a manner as to obtain very crystalline products, the mesoporosity is drastically reduced, but the replacement of diphosphonate groups with phosphite groups is also considerably reduced, thus reducing the microporosity in the interlayer region (see experimental example 2);

if operating in such a manner as to obtain semicrystalline products, as in the examples given in the cited patents), the percentage of diphosphonate groups replaced by phosphite groups can reach high values (about 30-35%, corresponding to a molar phosphite/diphosphonate ratio of 1:1), to therefore obtain a certain microporosity. However the micropore distribution is not narrow and the microporosity is always accompanied by a high degree of mesoporosity, which can be of the same order of magnitude as or even higher than the degree of microporosity (see experimental example 1).

It should be noted that if an attempt is made to increase the replacement of diphosphonate groups with phosphite groups by increasing the concentration of these latter in the synthesis solutions, solids are obtained which although having a high diphosphonate/phosphite molar ratio (1:4) are rather poor from the microporosity aspect. The reason for this seems to be that an excess of phosphorous acid in the synthesis solutions leads to the formation of compounds of the type already described in the case of zirconium phosphate-phosphite with asymmetric layers (G. Alberti, U. Costantino and G. Perego, J. Solid State Chem., 63, 455 (1986). In this respect, on the basis of the first diffraction maximum at 20.1 Å (FIG. 10) it is probable that the compounds obtained consist, as shown schematically in FIG. 4, of an interlayer region typical of zirconium diphosphonate-phosphite (distance 14.1 Å) and an interlayer region typical of zirconium phosphite (5.6 Å), so that the first maximum is obtained as the sum of the two interlayer distances. It is apparent that in such compounds most of the phosphite groups are localized in the interlayer regions typical of zirconium phosphite where, because of the total absence of diphosphonate groups, microporous cavities are not present. The microporosity is then restricted only to the diphosphonate-phosphite inner layer regions where however the phosphite/diphosphonate molar ratio is much lower than the total in the solid. This does not exclude however that in some of these compounds of low degree of crystallinity there may be a large quantity of mesopores in association with a modest microporosity. These results are rather deluding and agree with the fact that the zirconium diphosphonate-phosphite porosity distribution curves shown in the technical and patent literature on this subject up to the present time are all rather poor.

It has now been surprisingly found that the difficulties of the known art can be overcome if the synthesis is effected using, in mixture with phosphorous acid, particular diphosphonic acids carrying one ring or several linked ring, said ring or rings carrying side groups which increase their steric hindrance. In accordance therewith, the present invention relates to a tetravalent metal diphosphonate-phosphite composition definable by the following general formula:

$$M(O_3P-R-PO_3)_{1-x}(HPO_3)_{2x} \quad (I)$$

where:
M is a tetravalent metal;
x varies from 0.5 to 0.66;
R is an organic radical of bivalent aromatic type chosen from those definable by the following general formulas:

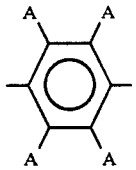  (II)

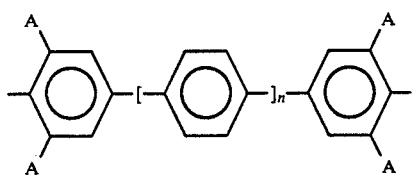  (III)

where: n varies from 0 to 2;
A is hydrogen or a group of medium steric hindrance chosen from —CH₃, —C₂H₅, —OH, —CH₂OH or another group of similar hindrance, with the condition that at least one A is other than hydrogen;

the composition also being in the form of a crystalline solid having the following characteristics:

type α layer structure with the diphosphonic groups positioned to join said layers together by a covalent bond (pillared compounds);

B.E.T. surface area from 300 to 500 m²/g depending on the degree of crystallinity and the nature of R in formula (I); and porosity in the micropore radius range of less than 20 Å (Angstrom), such micropores contributing to the extent of more than 95% of the total area for the most crystalline materials.

The tetravalent metal M in formula (I) can be chosen from zirconium, titanium and tin, and is preferably zirconium. In the preferred embodiment all the As in formulas (II) and (III) are other than hydrogen.

Specific examples of compositions which fall within formula (I) are the following:

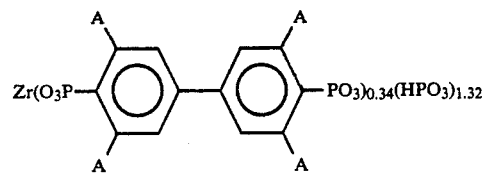

where A is as heretofore defined and the composition has a B.E.T. surface area of about 450 m²/g;

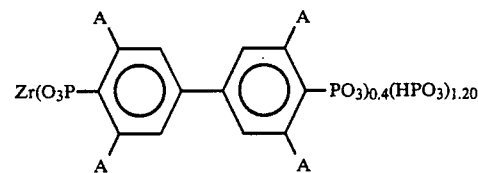

where A is as heretofore defined and the composition has a B.E.T. surface area of about 380 m²/g, micropores of radius less than 20 Å contributing more than 97% of the total area.

The present invention also relates to a process for preparing the aforedescribed diphosphonate-phosphite composition (I), comprising essentially reacting a diphosphonic acid (IIa) or (IIIa):

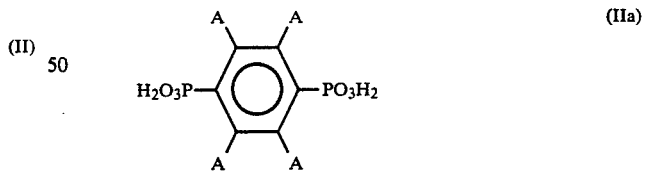  (IIa)

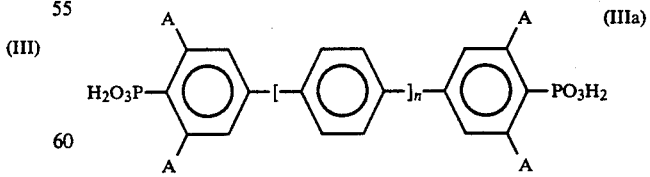  (IIIa)

where A and n have the aforesaid meaning, with phosphorous acid H₃PO₃ and with a soluble salt of a tetravalent metal, operating in a solvent consisting of dimethylsulphoxide/water containing hydrofluoric acid. The preferred tetravalent metal salt is zirconyl chloride octahydrate ZrOCl₂.8H₂O. The preferred diphosphonic acid (IIIa) is 4,4′-bis-phosphono-(3,3′,5,5′-tetramethyl)biphenyl acid.

The diphosphonic acids (IIa) and (IIIa) in which at least one A is other than hydrogen are new compounds and as such form an integral part of the present invention.

The reaction is performed with a molar ratio of phosphorus acids (diphosphonic acid IIa or IIIa plus phosphorous acid) to the tetravalent metal oxychloride of between 1 and 40. The hydrofluoric acid used can be a concentrated aqueous solution of the acid itself, with a molar ratio to the zirconium or other tetravalent metal of between 6 and 30. The reaction medium is important in the process of the present invention. Many of the solvents used in the known art adapt badly to the preparation of microporous compounds. On the other hand, particularly effective in obtaining the composition of the present invention are the sulphoxide solvents, especially dimethylsulphoxide in mixture with water. The reaction temperature can vary from 40° to 130° C. and the reaction time from 24 to 240 hours. Typically the reaction is performed at a temperature of the order of 80° C. for a time of about 120 hours. On termination of the reaction the tetravalent metal diphosphonate-phosphite composition (I) is recovered in the form of a microcrystalline solid by filtration or centrifuging, washed with organic solvent and dried.

It is not completely known why in the present invention the percentage of diphosphonic groups replaced by phosphite groups is much higher than that obtainable by using diphosphonic acids without lateral hindrance in the synthesis. For example in compositions with a medium degree of crystallinity, this percentage is about 66% (x=0.66). This result (see experimental example 4) is in itself interesting in that it enables the extent of porosity to be considerably increased in the interlayer region of zirconium diphosphonate-phosphites. However, the most surprising fact is that in contrast to that found with the other diphosphonic acids free of lateral hindrance, the phosphite percentage decreases very little as the degree of crystallinity increases. This peculiarity has enabled very crystalline compounds to be obtained, with a consequent very low level of mesoporosity, in which the percentage of disphosphonate groups replaced by phosphite groups is still around 60–62%. This high percentage of phosphite groups generates high microporosity in the interlayer region, it having also been found experimentally (see experimental example 5) that the microscope distribution is very narrow. In practice the most crystalline compounds have only a narrow microporosity distribution, which indicates regular phosphite group distribution in the crystalline structure. Consequently the results obtained, in exceeding the limits of the known art, represent fundamental progress in the field of pillared tetravalent metal diphosphonate compositions, with therefore highly potential application in gaseous mixture separation and in shape selective catalysis.

Without wishing to enforce a particular theory, it is considered that the presence of steric "A" groups in the diphosphonic acid hinders or prevents the formation of the compound with the zirconium is that the hindering diphosphonic groups are hindered or prevented from lying at a distance of 5.3 Å, characteristic of the α phase (FIG. 2). The presence of small $O_3P$-R groups such as phosphite, favours a situation, independently of the degree of crystallization, in which groups of small steric hindrance are situated about each hindering diphosphonic group. FIG. 5a shows an example of a hypothetical structural model, seen from above, of the compound zirconium 4,4′(3, 3′,5,5′-tetramethyl) biphenyldiphosphonate-phosphite. In this figure the dashed circumferences and the internal circles indicate respectively the maximum and minimum hindrance (Van der Waals) of the diphosphonic group under consideration. It is interesting to note that in this model each diphosphonic group is surrounded by six phosphite groups and that the distance between the centres of two adjacent pillars is 9.2 Å along the direction b, and 15.9 Å along the direction a. A lateral view of this model, relative to only a single row of diphosphonate-phosphites along the a axis is shown schematically in FIG. 5b. It can be seen that the ideal structure indicates a diphosphonate/-phosphite molar structure of 1:4, corresponding to 66% of diphosphonic groups replaced by phosphite, this percentage being very close to that found experimentally (see experimental examples 4 and 5).

The following experimental examples are given to better illustrate the present invention.

EXAMPLE 1 (comparison)

Preparation and porosity of zirconium biphenyl diphosphonate-phosphite with a low degree of crystallinity 0.44 g of 4,4'-biphenyl diphosphonic acid (prepared as described in U.S. patent application Ser. No. 738,891 now U.S. Pat. No. 5,166,380,) and 5.63 g of phosphorous acid (reagent C. Erba RPE) are dissolved in 22 ml of DMSO (dimethylsulphoxide) (C. Erba RPE) contained in a plastic vessel. 0.45 g of $ZrOCl_2.8H_2O$ (Merck, proanalysis RPE) dissolved in 3 ml of concentrated HF (50% by weight, C. erba) are added to the clear solution maintained at 80° C. The solid obtained after 24 hours is separated from the solution by centrifuging, washed twice with about 50 ml of DMSO and 3 times with about 50 ml of acetone, and finally dried in an oven at 60° C. The solid zirconium diphosphonate-phosphite obtained in this manner is stored in a vacuum drier containing phosophoric anhydride.

Figure 6:
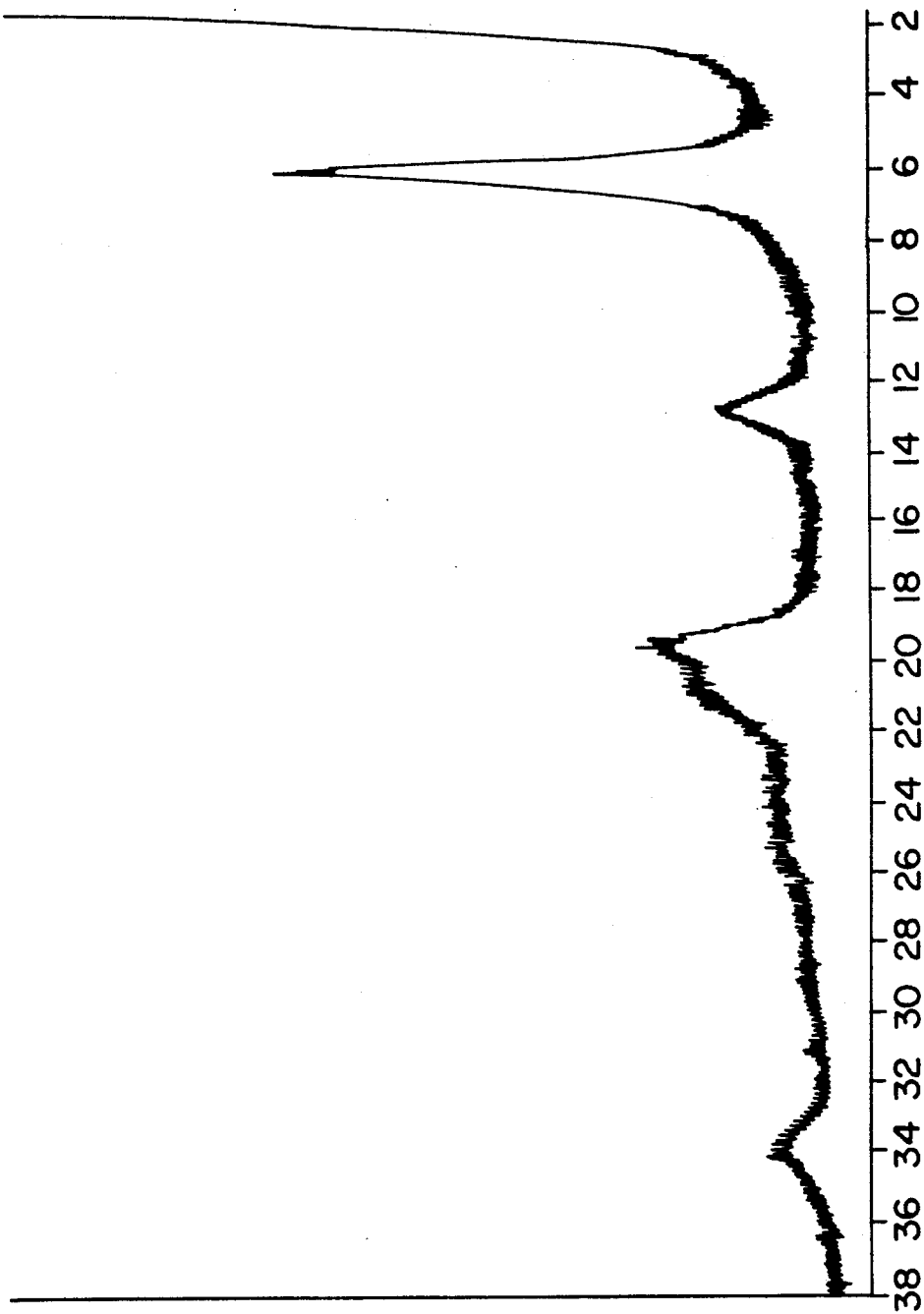
FIG. 6 shows the X-ray diffraction spectrum of the zirconium biphenyl diphosphonate-phosphite powder described in Example 1.

The X-ray diffraction spectrum of the powder (Ni-screened CuKα radiation, tube feed 40 KV, 20 mA, goniometer scanning rate 2°/min) indicated in FIG. 6 shows reflexes typical of a type α structure and shows an interlayer distance of 14 Å. To derive the diphosphonate/phosphite molar ratio of the solid, $^{31}p$ nuclear magnetic resonance is used. About 20 g of solid are dissolved in a few drops of concentrated hydrofluoric acid, taken up in 1 ml of DMSO and analyzed with a Bruker 200 spectrometer. The molar ratio is 1:1, corresponding to about 33% of diphosphonate pillars replaced by phosphite.

Figure 7A:
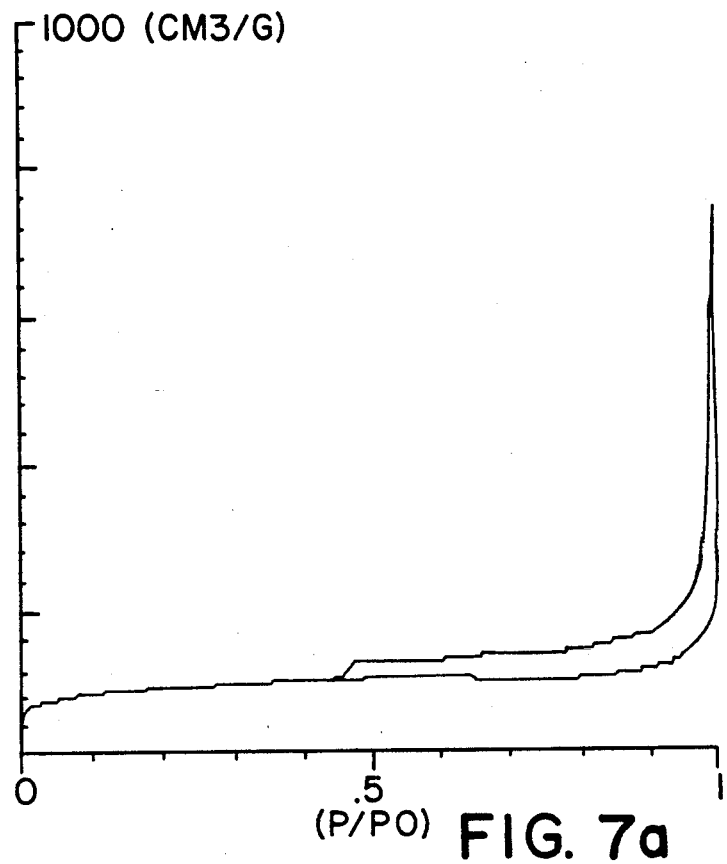
FIG. 7 is a porosimetric characterisation of the zirconium biphenyl diphosphonate-phosphite described in Example 1, showing a) the nitrogen adsorption and deadsorption isotherm, and b) the porosity distribution curve.
Figure 7B:
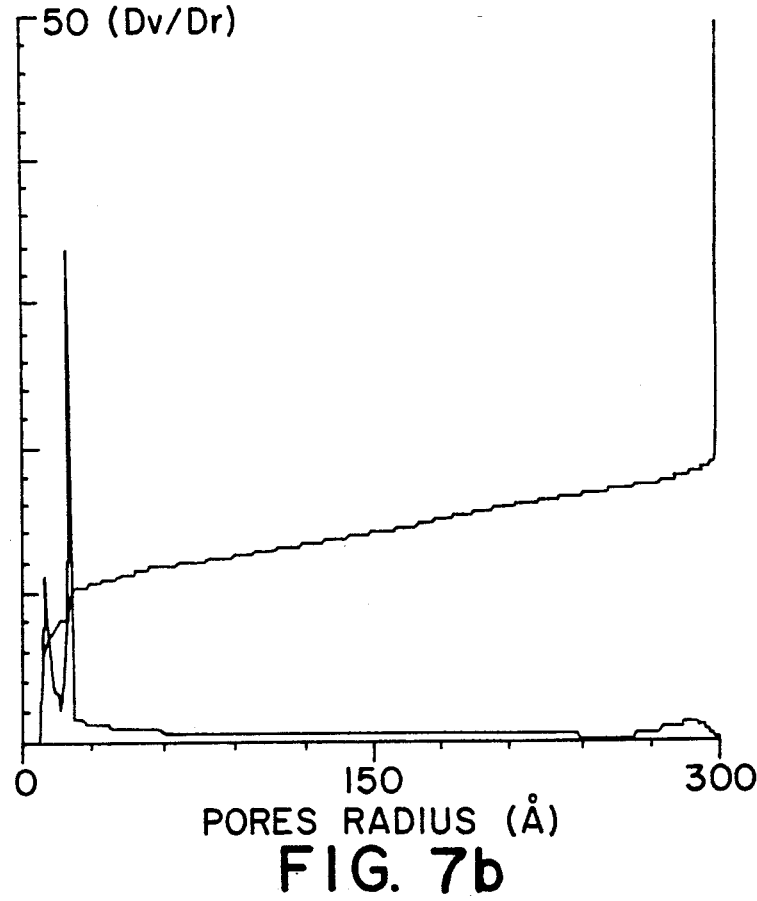

To obtain the porosity characteristics the solid is firstly degassed at a temperature of 125° C. and a pressure of $5 \times 10^{-3}$ torr for 6 hours. A surface area measurement is then made by nitrogen adsorption at −195° C., by means of a C. Erba Sorpomatic 1800 instrument controlled by a computer using a C. Erba "Erbacard" electronic card and a "Milestone 100" program. The adsorption and desorption isotherm shown in FIG. 7a indicates a significant hysteresis typical of mesoporous solids. The mathematical treatment of the isotherm in accordance with the B.E.T. theory gives a surface area of 270 $m^2/g$ and the pore distribution curve (FIG. 7b) shows a single intense maximum corresponding to pores of radius 22 Å. From this curve it is calculated that the pore fraction lying within the range 15–30 Å is about 30% of the total.

EXAMPLE 2 (comparison)

Preparation and porosity of zirconium biphenyl diphosphonate-phosphite with a greater degree of crystallinity To obtain a greater degree of crystallinity the procedure of Example 1 is followed but the HF concentration is increased and a few ml of water are added to increase the activity of this complexing agent. The increased complexing of the zirconium considerably slows the precipitation of the zirconium diphosphonate-phosphite, so increasing the degree of crystallinity.

Figure 8:
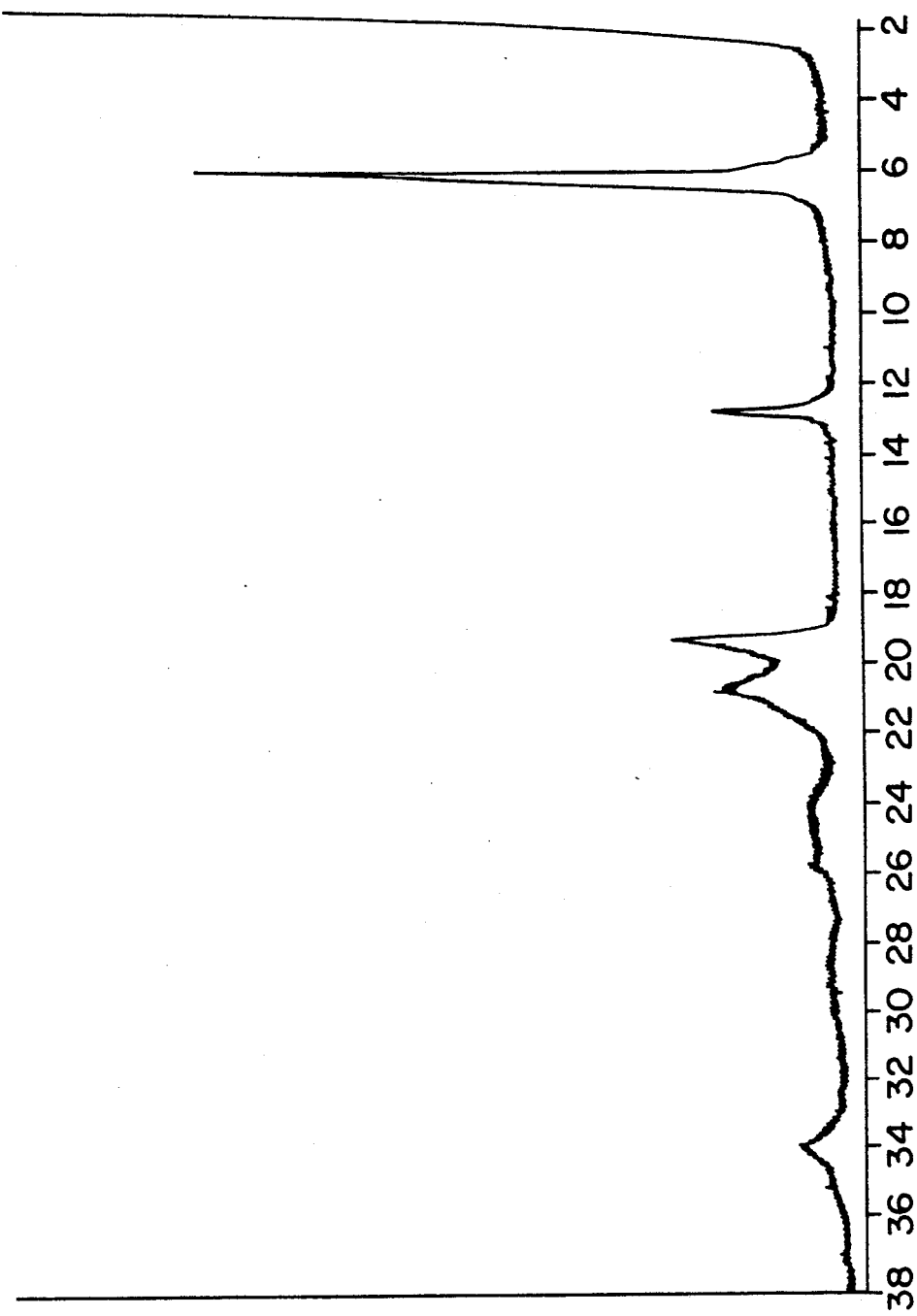
FIG. 8 shows the X-ray diffraction spectrum of the zirconium biphenyl diphosphonate-phosphite powder described in Example 2.

Specifically, 0.44 g of 4,4'-biphenyl diphosphonic acid and 11.37 g of phosphorous acid are dissolved in 10 ml of DMSO and 11.2 ml of water, contained in a plastic vessel. 0.45 g of $ZrOCl_2.8H_2O$ dissolved in 3.8 ml of concentrated HF and 1.2 ml of water are added to the clear solution maintained at 80° C. The solid obtained after 4 days is separated, washed, dried and analyzed as described in Example 1, to show a diphosphonate/phosphite molar ratio of 1:0.15 corresponding to about 7% of diphosphonate pillars replaced by phosphite. The powder X-ray diffraction spectrum, shown in FIG. 8, is similar to that of the compound prepared in Example 1 (FIG. 6). However the diffraction reflexes are narrower and better resolved, indicating a greater crystallinity of the compound.

Figure 9A:
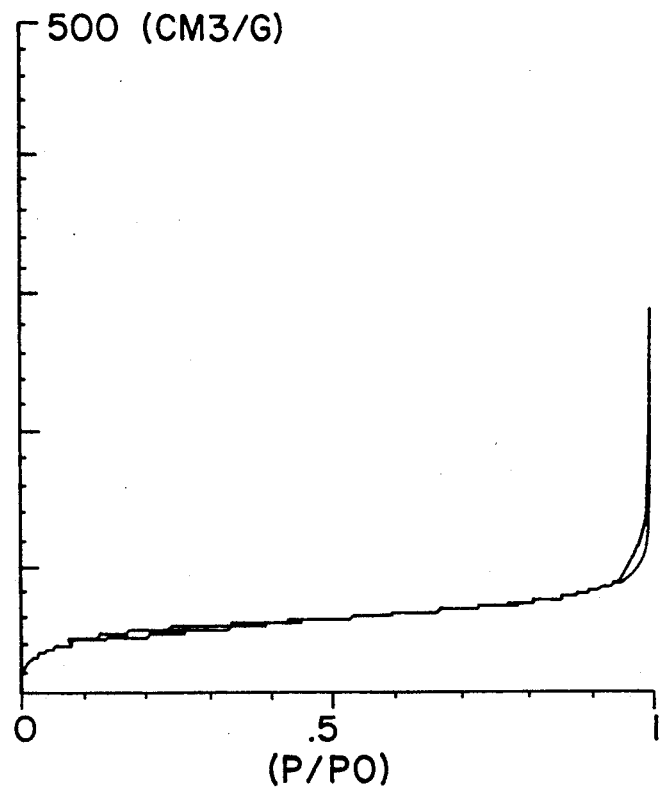
FIG. 9 is a porosimetric characterisation of the zirconium biphenyl diphosphonate-phosphite described in Example 3, showing a) the nitrogen adsorption and deadsorption isotherm, and b) the porosity distribution curve.
Figure 9B:
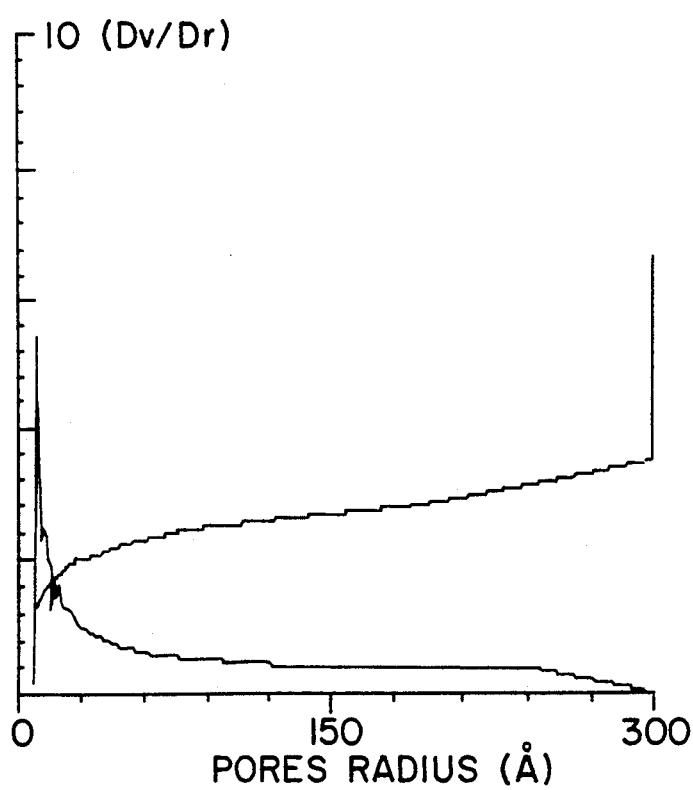

The surface area measurement shows 85 $m^2/g$ and a pore distribution curve of statistical type (FIG. 9b).

EXAMPLE 3 (comparison)

Figure 1:
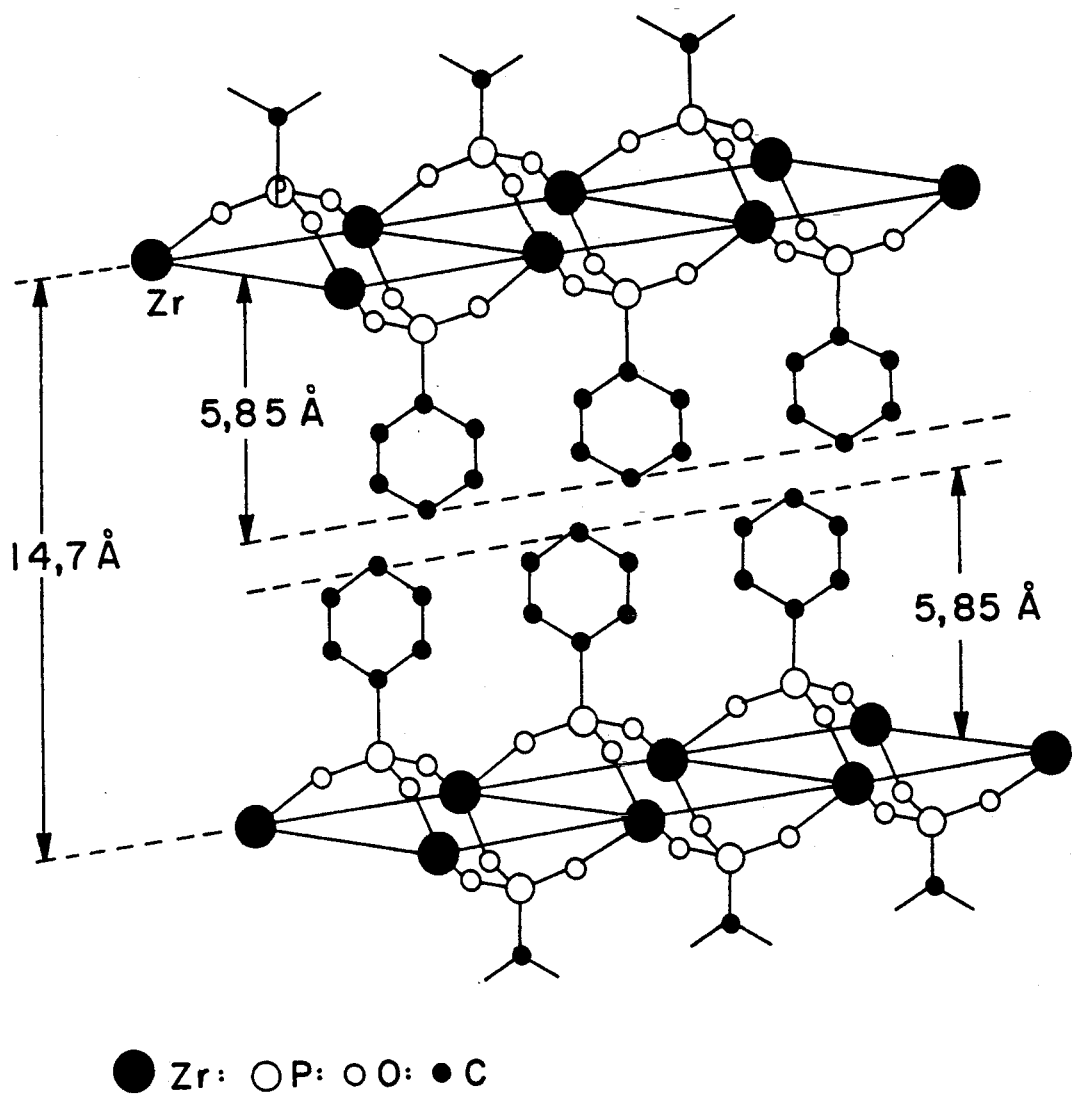
FIG. 1 is a schematic representation of the structure of zirconium benzenephosphonate.
Figure 2:
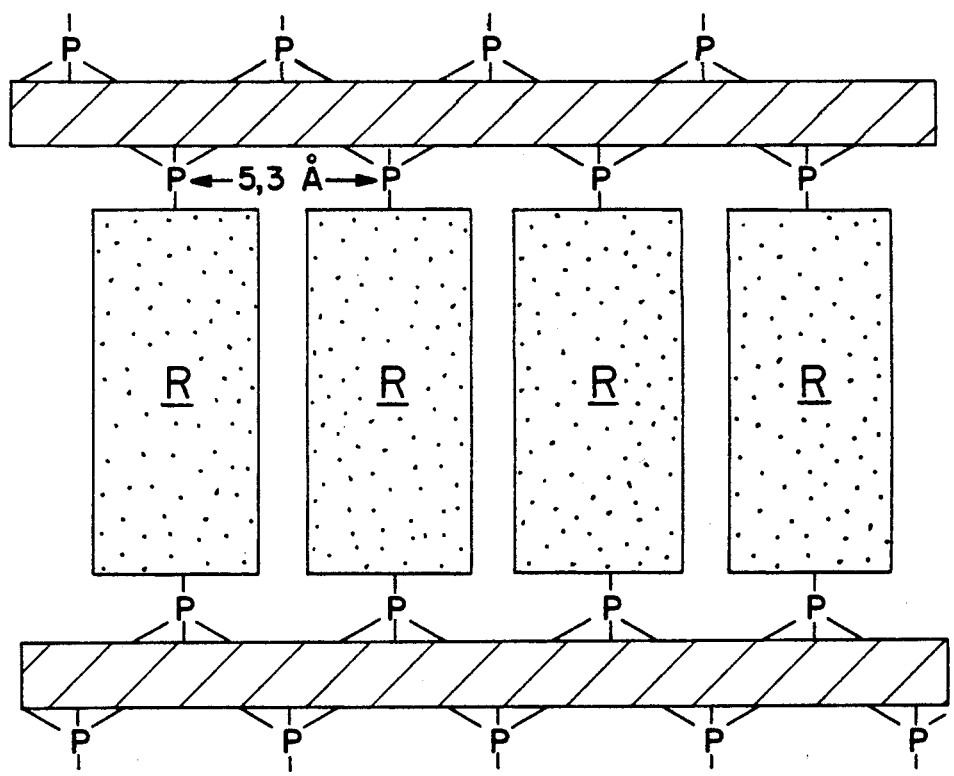
FIG. 2 is a schematic representation of the structure of a pillared tetravalent metal diphosphonate.
Figure 3:
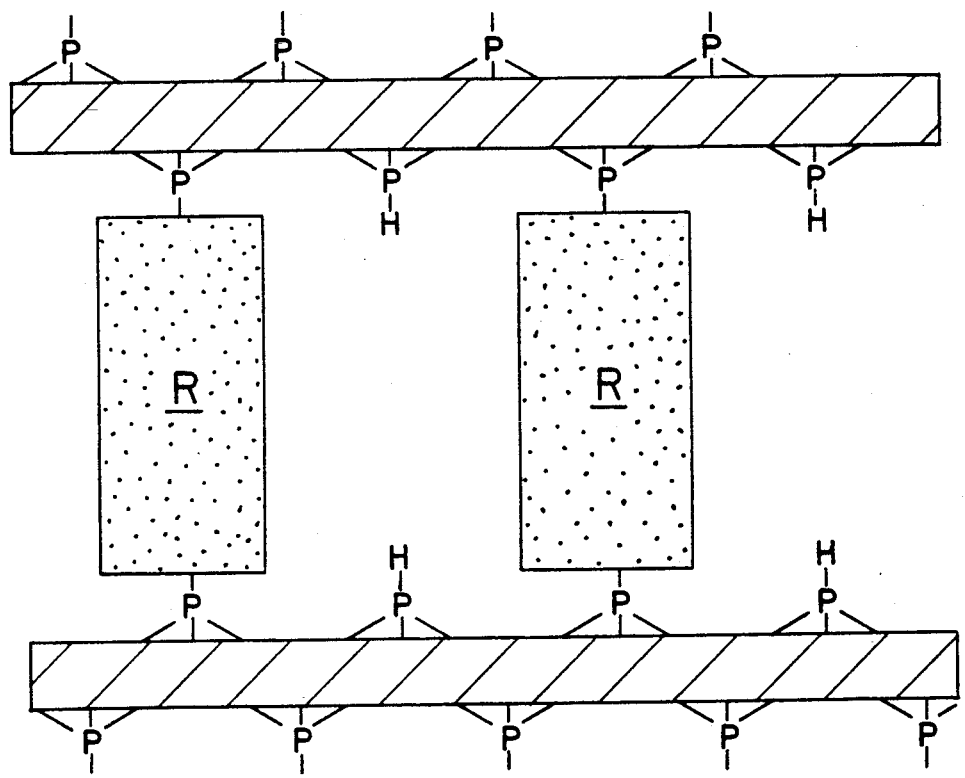
FIG. 3 is an idealized schematic representation of the structure of a pillared zirconium diphosphonate-phosphite.
Figure 4:
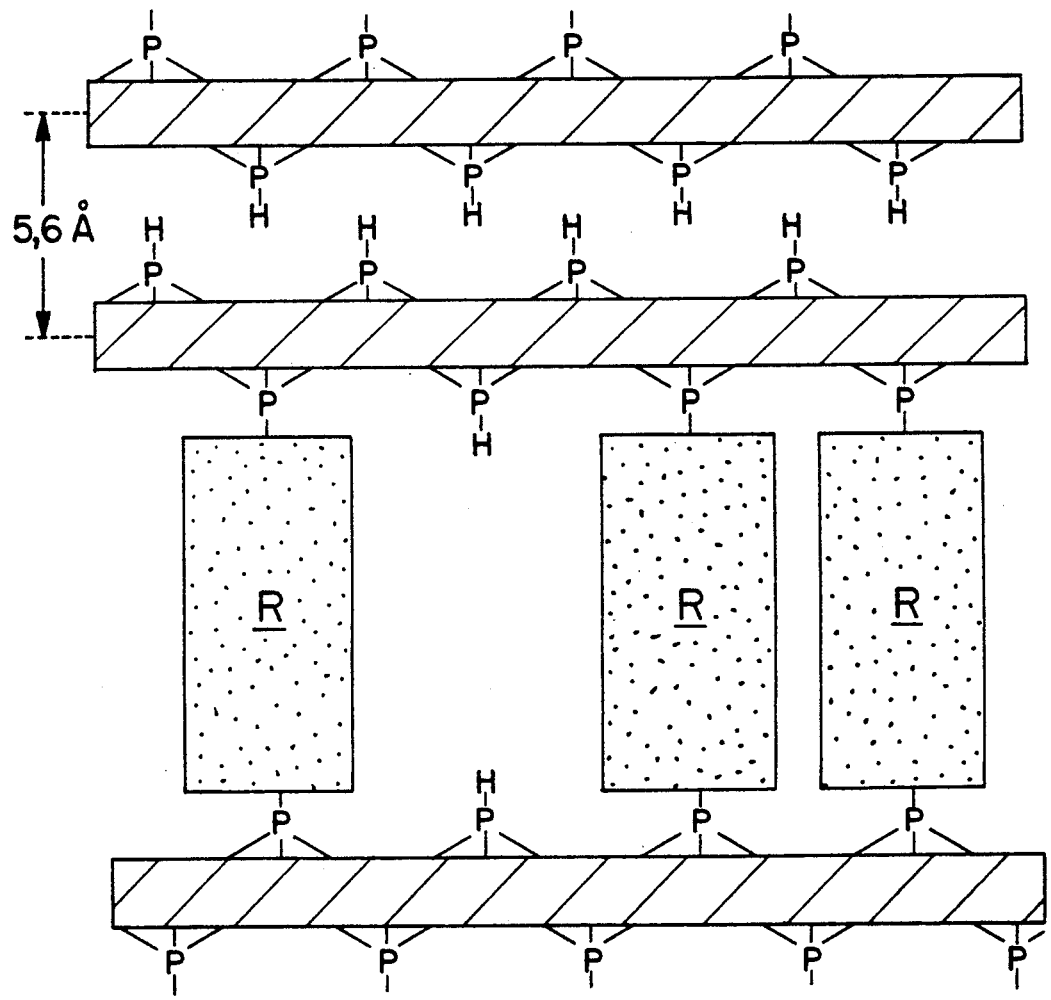
FIG. 4 is a schematic representation of the structure of a pillared zirconium diphosphonate-phosphite showing the asymmetry phenomenon in the composition of the layers.
Figure 5A:
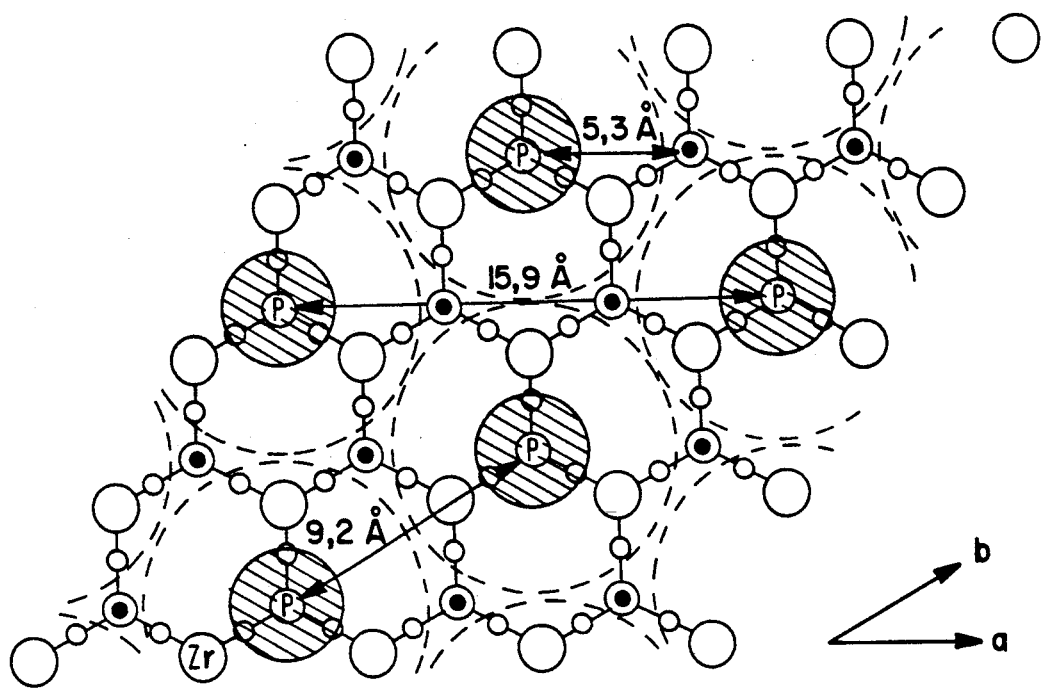
FIG. 5 is a hypothetical structural model of zirconium 4,4′(3, 3′,5,5′-tetramethyl) biphenyl-diphosphonate-phosphite in a) top view and b) side view.
Figure 5B:
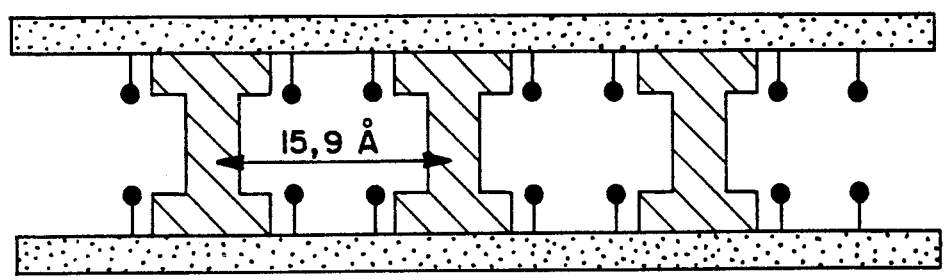
Figure 10:
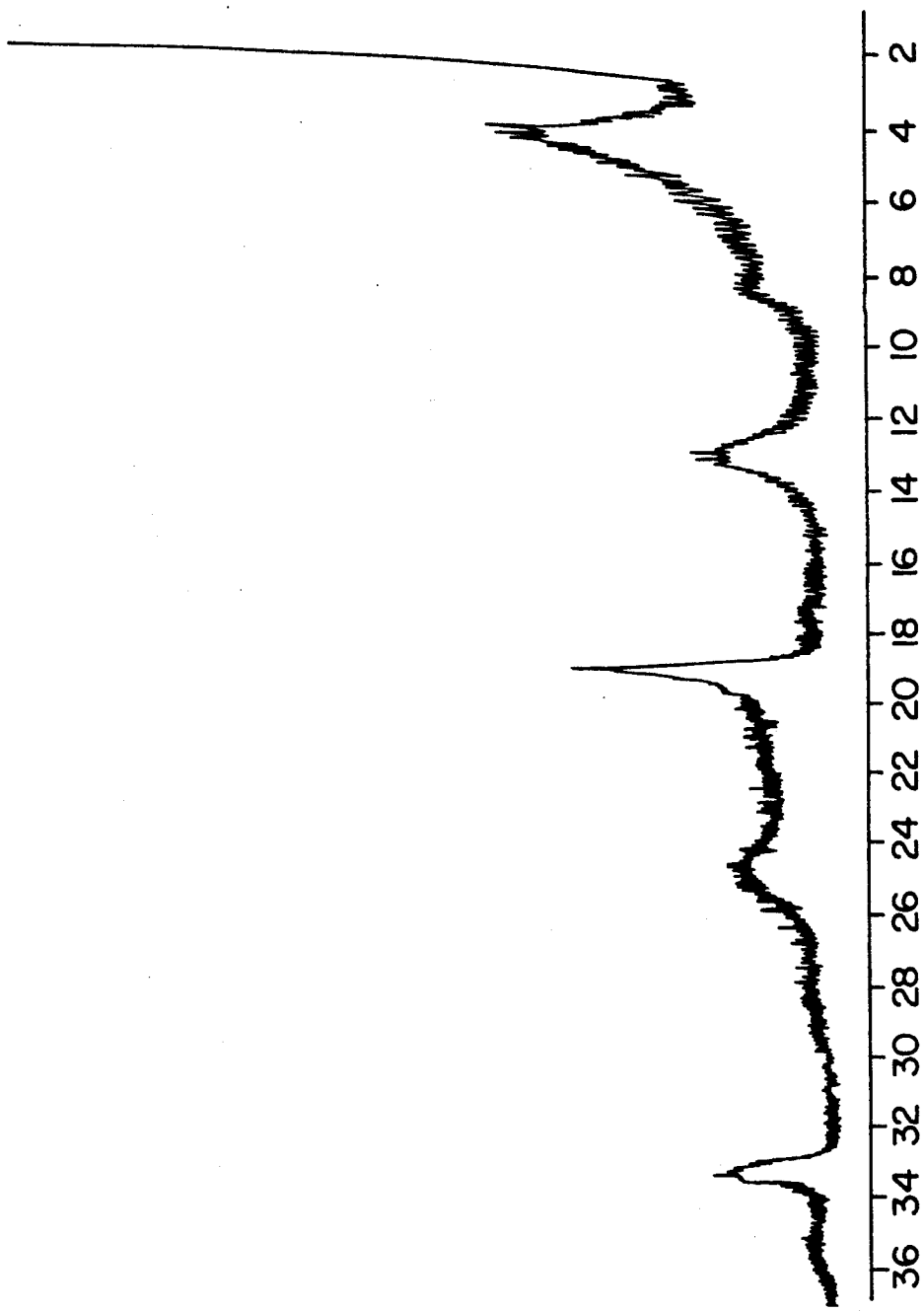
FIG. 10 shows the X-ray diffraction spectrum of the zirconium biphenyl diphosphonate-phosphite powder described in Example 3.

Preparation and porosity of zirconium biphenyl diphosphonate-phosphite with a high degree of crystallinity 0.40 g of 4,4'-biphenyl diphosphonic acid and 55.2 g of phosphorous acid are dissolved in 52 ml of DMSO and 75 ml of water, contained in a plastic vessel. 0.42 g of $ZrOCl_2.8H_2O$ dissolved in 3.2 ml of concentrated HF are added to the clear solution maintained at 80° C. The solid obtained after 7 days is separated, washed, dried and analyzed as described in Example 1, to show a diphosphonate/phosphite molar ratio of 1:4 and an interlayer distance of 20.1 Å (diffraction spectrum shown in FIG. 10). The composition data and the value of the interlayer distance can be interpreted as the formation of a phase with asymmetric layers [see G. Alberti, U. Costantino and G. Perego, J. Solid State Chem., 63, 455 (1986] in which interlayer regions containing phosphite groups alternate with regions containing phosphonate groups with dissolved phosphite groups (see FIG. 4).

EXAMPLE 4

Preparation and porosity of zirconium 4,4'(3,3',5,5'-tetramethyl) biphenyl-diphosphonate-phosphite with a low degree of crystallinity a) Preparation of 4,4'-dibromo-3,3',5,5'-tetramethyl biphenyl 32 g (312 mmoles) of t-BuONO and 75 ml of bromoform are placed in a 500 ml two-neck flask fitted with a mechanical stirrer, condenser, dropping funnel and heating bath. 25 g (104 mmoles) of 3,3',5,5'-tetramethyl-benzidine dissolved in 175 ml of bromoform are added to the mixture heated in an inert atmosphere to 65° C. under stirring. The resultant mixture is left stirring at 65° C. for 2 hours and is then filtered. The precipitate is washed with ethyl ether, the used wash liquid together with the filtrate then being evaporated to dryness.

The residue is then dissolved in 70 ml of ethyl acetate and chromatographed in a silica gel column of 2.5 litres volume, eluting with petroleum ether. A single fraction having a volume of 6 liters is recovered, from which 31 g of still crude product are recovered after evaporation. Repetition of the purification procedure under the stated conditions leads to the recovery of 16.5 g of the desired product, with a molar yield of 43%.

Analysis: TLC-Silica F (petroleum ether/ethyl acetate 75:25).

$^1$H-NMR (DMSO-D$_6$): δ 2.42 (s, 12H, CH$_3$); 7.51 (s, 2H, aromatic) IR and MS in accordance with the structure.

b) Preparation of 4,4'-bis-diethylphosphonate (3,3',5,5'-tetramethyl) biphenyl 4.37 g (182 moles) of NaH are added under mechanical stirring in an inert atmosphere to a solution of 23.1 ml (179.3 mmoles) of diethyl phosphite in 80 ml of hexamethyl phosphotriamide. After heating the mixture to 70° C. for 30 minutes (until gas is evolved), 34 g (179.3 mmoles) of CuI and 16.5 g (44.8 mmoles) of 4,4'-dibromo(3,3',5,5'-tetramethyl) biphenyl are added. The mixture is heated under stirring to 160° C. for 2 hours, then cooled to ambient temperature and diluted with 1000 ml of diethyl ether and 800 ml of water. After stirring for about one hour, the mixture is filtered through a Gooch crucible and the precipitate washed with diethyl ether. The filtrate, placed in a separator funnel, separates into the two phases and the water phase is extracted with diethyl ether (2×200 ml). The pooled organic extracts are washed with water (150 ml), dried over anhydrous sodium sulphate and evaporated to dryness under vacuum, to obtain 24.4 g of crude product. This crude product is dissolved in 100 ml of ethyl acetate and applied to a 2.5 liter chromatographic silica gel column, and eluted with ethyl acetate (total eluate volume 7 liters). 9.0 g of the desired product are recovered, with a molar yield of 42.3%.

Analysis:
TLC-Silica F [(a) petroleum ether/ethyl acetate 75:25; (b) ethyl acetate 100%].

$^1$H-NMR (CDCl$_3$): δ 1.33 (t, 12H, CH$_3$CH$_2$); 2.71 (d, 12H, CH$_3$); 4–4.3 (m, 8H, CH$_2$); 7.30 (4H, aromatic).

MS-EI: (M+) 482; m/e 467, 439, 411, 373, 351, 333, 271.

c) Preparation of 4,4'-bis phosphono (3,3',5,5'-tetramethyl) biphenyl acid 85 ml of 33% HBr in acetic acid (4.1M) are added under magnetic stirring to 8 g (16 mmoles) of 4,4'-bis diethyl phosphonate (3,3',5,5'-tetramethyl) biphenyl. The mixture is heated to 80° C. for 4 hours, the apparatus being fitted with a cold condenser (ethanol/dry ice) to prevent loss of HBr. 200 ml of water re added to the mixture after cooling. The precipitate formed is filtered off, washed on the filter with iced water and dried under vacuum (20 mm Hg) at 50° C. overnight. 5.79 g of the desired product are obtained, with a molar yield of 94%.

Analysis:
TLC-Silica F-eluent CH$_3$CN-H$_2$O 75:25).

$^1$H-NMR (DMSO-D$_6$): δ 2.65 (s, 12H, CH$_3$); 7.40 (4H, aromatic).

Figure 11:
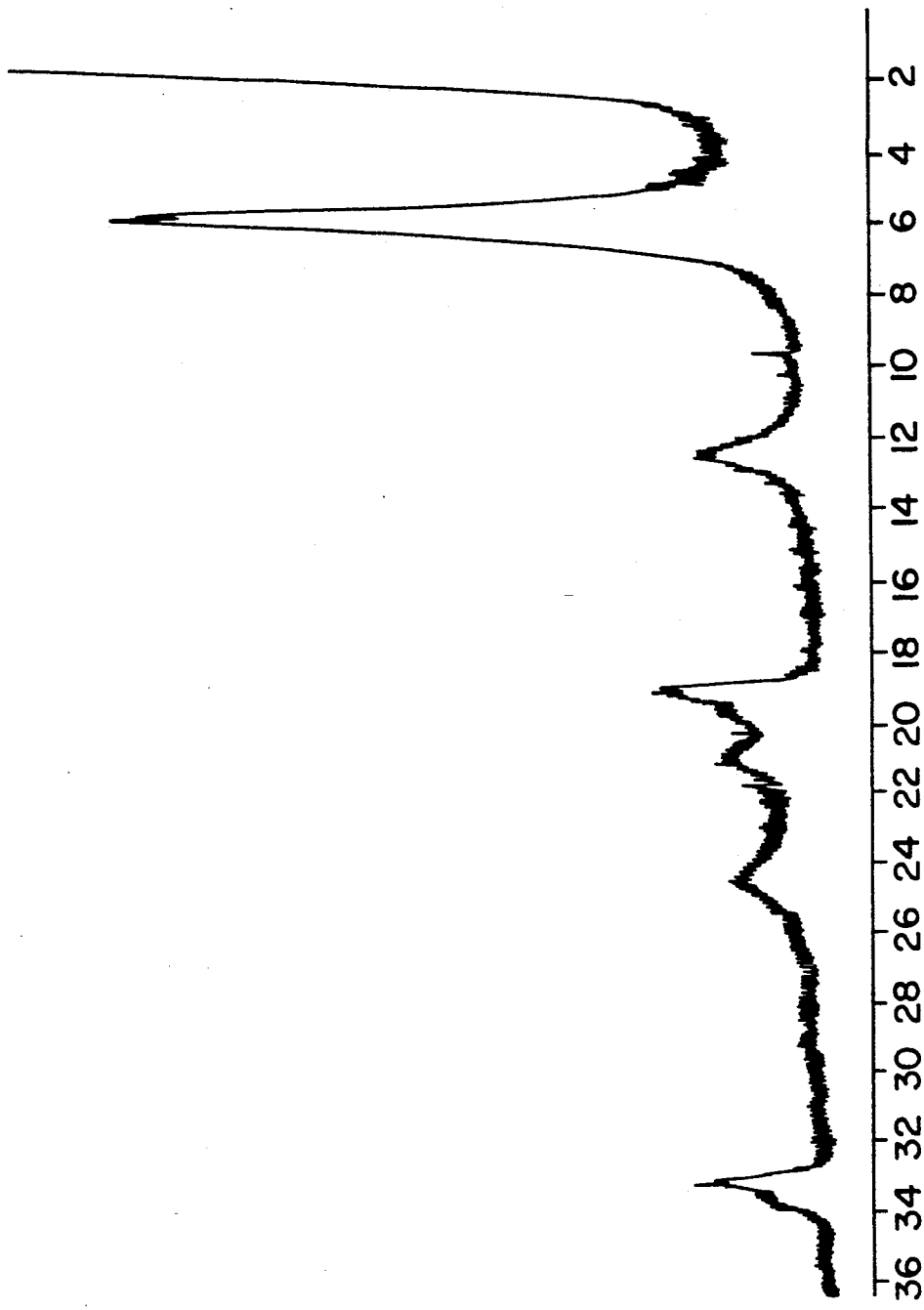
FIG. 11 shows the X-ray diffraction spectrum of the zirconium 4,4′(3,3′,5,5′-tetramethyl) biphenyl-diphosphonate-phosphite powder described in Example 4.

$^{31}$P-NMR (DMSO-D$_6$): δ 17.02. External reference H$_3$PO$_4$ MS FAB (±) and IR in accordance with the structure.

d) Preparation of zirconium diphosphonate-phosphite 0.19 g of 4,4'-bis-phosphono(3,3',5,5'-tetramethyl) biphenyl acid (prepared as heretofore described) and 0.74 g of phosphorous acid are dissolved in 18 ml of DMSO contained in a plastic vessel maintained at a temperature of 80° C. (to facilitate complete dissolution the mixture can be subjected to sonication for a few minutes). 0.80 g of ZrOCl$_2$.8H$_2$O dissolved in 1.5 ml of concentrated HF and 1 ml of water are added to the clear solution. The solid obtained after 24 hours is separated, washed, dried and analyzed as described in Example 1, to show a diphosphonate/phosphite molar ratio of 1:3.5, corresponding to about 64% of diphosphonate pillars replaced by phosphite and an interlayer distance of 14.2 Å (diffraction spectrum shown in FIG. 11). The surface area measurement gives a value of 450 m$^2$/g.

Figure 12A:
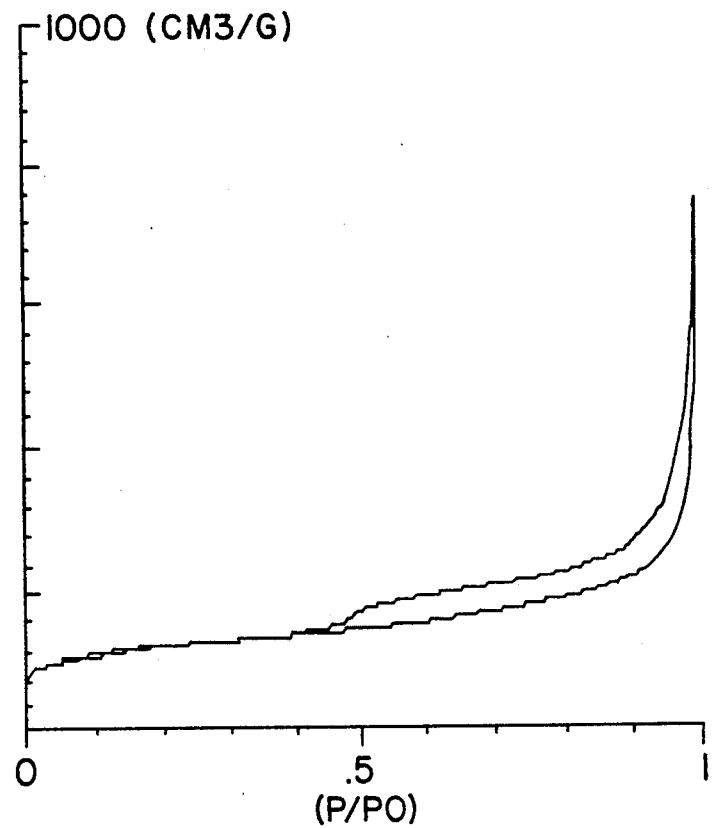
FIG. 12 is a porosimetric characterisation of the zirconium 4,4′(3,3′,5,5′-tetramethyl) biphenyl-diphosphonate-phosphite described in Example 4, showing a) the nitrogen adsorption and deadsorption isotherm, and b) the porosity distribution curve.
Figure 12B:
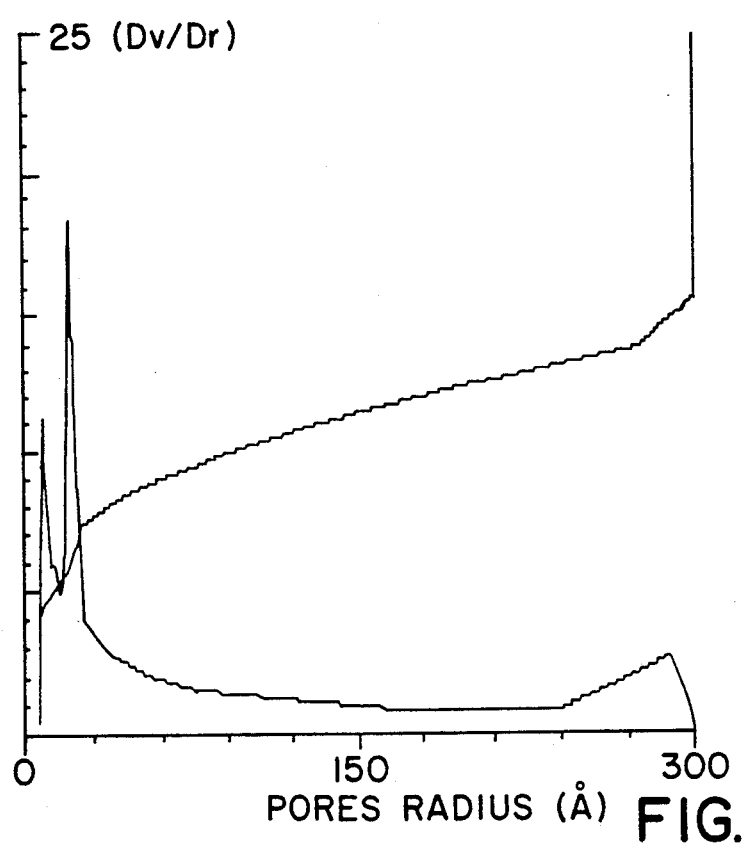

The porosity distribution shows an intense maximum for a pore radius of 22 Å. From this curve it can be calculated that about 20% of the total porosity is concentrated between 15 and 30 Å (adsorption-desorption isotherm and pore distribution shown in FIGS. 12a and 12b).

EXAMPLE 5

Preparation and porosity of the zirconium diphosphonate-phosphite of the preceding example but with a high degree of crystallinity To increase the degree of crystallinity of the zirconium diphosphonate-phosphite of the preceding example, the procedure described in the publication of G. Alberti, U. Costantino and R. Giulietti in J. Inorg. Nucl. Chem., 42, 1062 (1980) is followed, in which the zirconium is slowly decomplexed by the fluoro complex by means of a gradual increase in temperature. Specifically, 1.04 g of 4,4'-bis-phosphono(3,3', 5,5'-tetramethyl) biphenyl (prepared as described in Example 4) and 4.14 g of phosphorous acid are dissolved in 28 ml of DMSO and 6 ml of water contained in a plastic vessel maintained at a temperature of 70° C. 0.60 g of ZrOCl$_2$.8H$_2$O dissolved in 1.6 ml of concentrated HF and 4.4 ml of water are added to the clear solution maintained at a temperature of 70° C. The solution remains clear and has the following composition: [(CH$_3$)$_4$C$_{12}$H$_4$(PO$_3$H$_2$)$_2$]=0.07M; [H$_3$PO$_3$]=1.26M; [Zr$^{IV}$]=0.05M; [HF]=1.17M.

The vessel is closed and the temperature of the temperature-controlled bath raised at a rate of about 5° C./hour until the initial solution turbidity disappears. The temperature is then lowered by 5° C. and then allowed to rise slowly in a uniform manner (2° C./day) to about 95° C.

Figure 13:
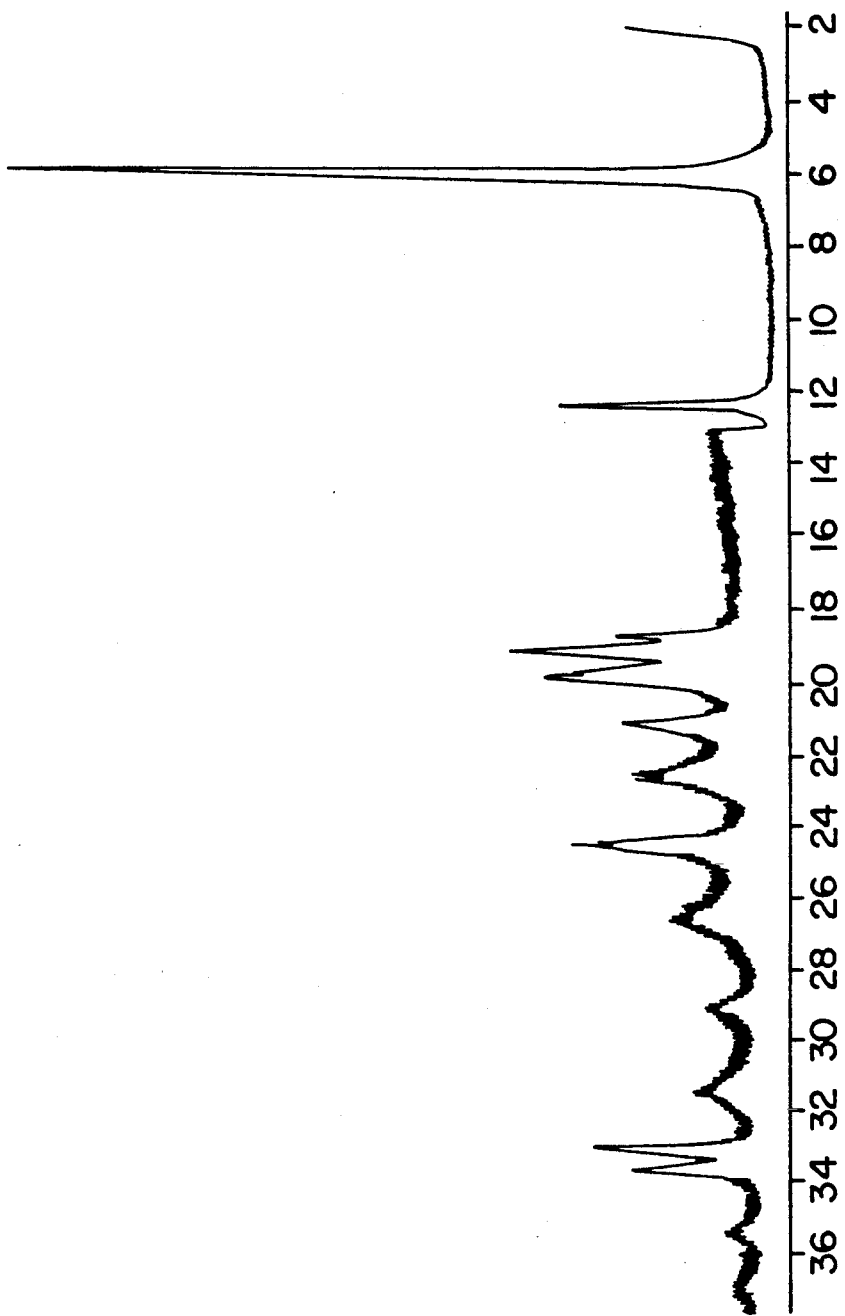
FIG. 13 shows the X-ray diffraction spectrum of the zirconium 4,4′(3,3′,5,5′-tetramethyl) biphenyl-diphosphonate-phosphite powder described in Example 5.
Figure 14A:
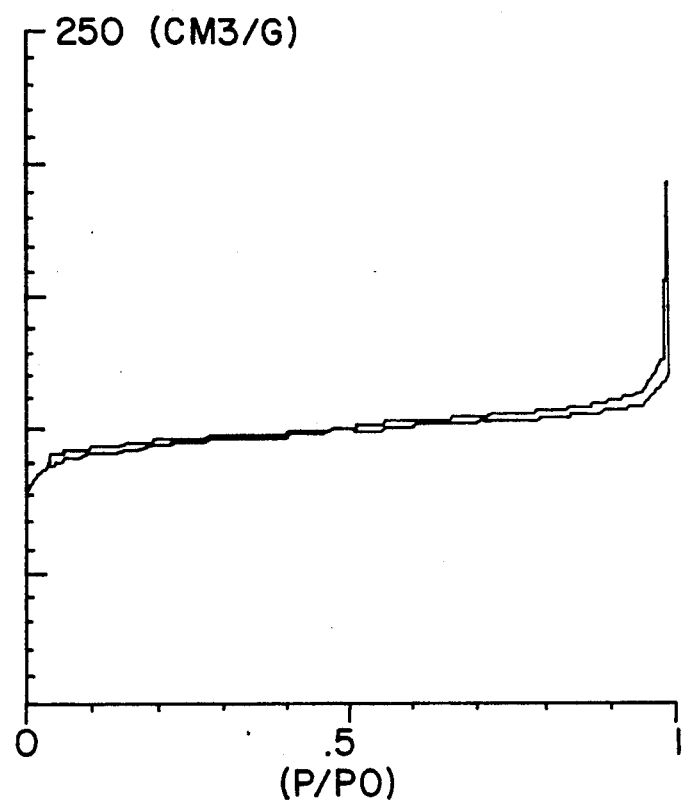
FIG. 14 is a porosimetric characterisation of the zirconium 4,4′(3, 3′,5,5′-tetramethyl) biphenyl-diphosphonate-phosphite described in Example 5, showing a) the nitrogen adsorption and deadsorption isotherm, and b) the porosity distribution curve.
Figure 14B:
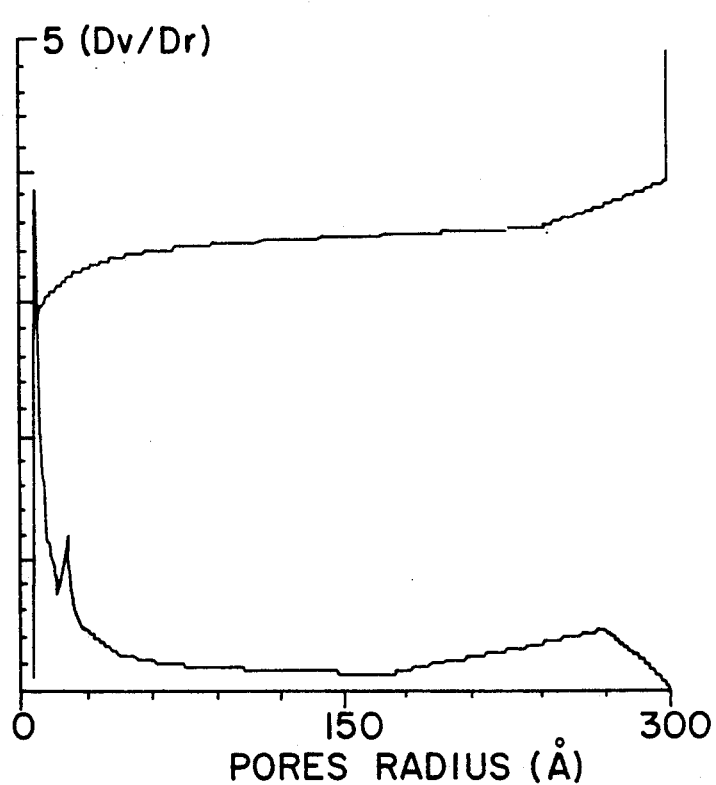

The microcrystalline solid which forms is separated, washed, dried and analyzed as described in Example 1 to show a diphosphonate/phosphite molar ratio of 1:3, corresponding to about 60% of diphosphonate pillars replaced by phosphite and an interlayer distance of 14.2 Å. The diffraction spectrum shown in FIG. 13 clearly illustrates a high degree of compound crystallinity. The weight loss curve derived by heating the sample in a thermobalance at a heating rate of 3° C./minute shows that the sample begins to decompose at a temperature between 250° and 300° C. The adsorption and desorption isotherm of FIG. 14a shows a light hysteresis. Mathematical treatment of the data in accordance with the B.E.T theory suggests a surface area of 380 m$^2$/g, and the pore distribution curve (FIG. 14b) shows a single very contained maximum corresponding to pores of 22 Å radius. From this curve it is calculated that the porosity formation within the range of 20–30 Å is less than 5% of the total porosity. Mathematical treatment of the isotherm by the Dubinin theory gives a micropore volume of 0.15 ml/g. By subtracting the micropore contribution to the total adsorption the "reduced" isotherm can be constructed, shown in FIG. 15b. The surface area calculated from this curve is 10 m$^2$/g without considering the micropore contribution. The porosity data are confirmed experimentally by the n-nonane preadsorption method, as described by S. J. Gregg and M. M. Tayabb in J. Chem. Soc. Faraday Trans. I. 74, 349 (1978). The sample for which the surface area is to be determined is firstly degassed at 125° C., then left in contact with n-nonane vapour (C. Erba RPE) in a vacuum line, and then again degassed at 25° C. and $10^{-6}$ torr for 6 hours. Under these conditions only the nonane adsorbed in the micropores (dimensions less than 10–15 Å) is not removed. A second surface area measurement and mathematical treatment of the data by the B.E.T. theory gives a value of 6 $m^2/g$.

Figure 15:
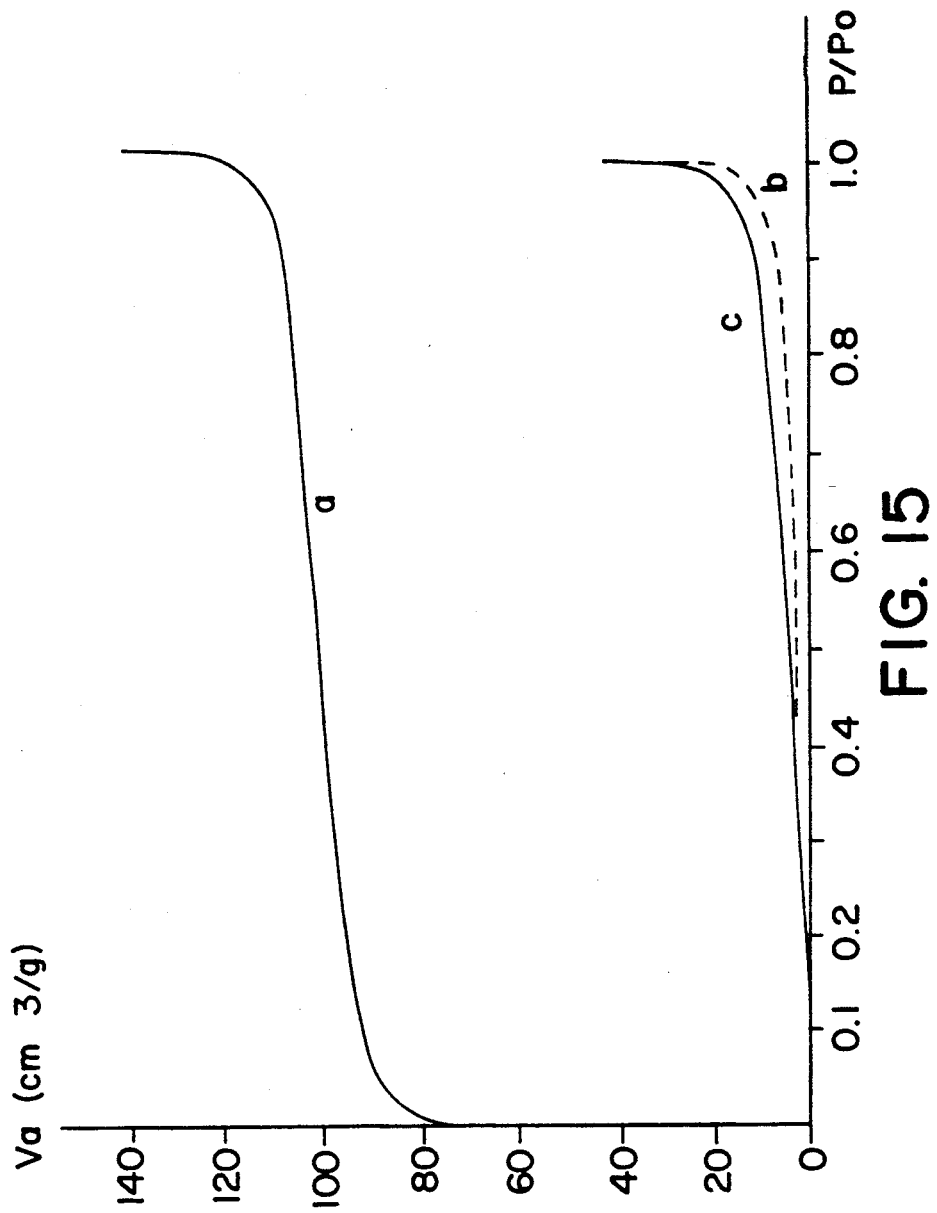
FIG. 15 is a comparison between the adsorption isotherms of zirconium 4,4'(3,3',5,5'-tetramethyl) biphenyl-diphosphonete-phosphite described in Example 5, showing a) the adsorption isotherm of the non-pretreated material, b) the "reduced" adsorption isotherm, and c) the adsorption isotherm of the material pretreated with n-nonane.

The new adsorption isotherm is shown in FIG. 15c. From the difference between the curve relative to the original compound (shown for comparison in FIG. 15a) and this new curve it can be calculated that the micropore volume is 0.15 ml/g. From these data it can be calculated that the micropores contribute more than 97% of the total surface area.

We claim:

1. A tetravalent metal diphosphonate-phosphite composition definable by the following general formula:

$$M(O_3P-R-PO_3)_{1-x}(HPO_3)_{2x} \qquad (I)$$

where:
 M is a tetravalent metal;
 x varies from 0.5 to 0.66;
 R is an organic radical of bivalent aromatic type chosen from those definable by the following general formulas:

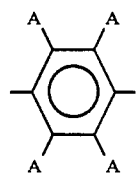

(II)

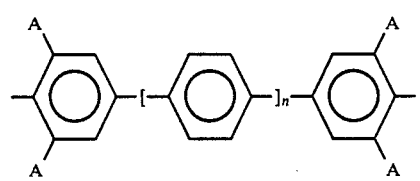

(III)

where: n varies from 0 to 2;
 A is hydrogen or a group of medium steric hindrance chosen from $-CH_3$, $-C_2H_5$, $-OH$, $-CH_2OH$ or another group of similar hindrance, with the condition that at least one A is other than hydrogen;
the composition also being in the form of a crystalline solid having the following characteristics:
 type $\alpha$ layered structure with the diphosphonic groups positioned to join said layers together by a covalent bond (pillared compounds);
 B.E.T. surface area from 300 to 500 $m^2/g$ depending on the nature of R in formula (I); and
 porosity in the micropore radius range of less than 20 Å (Angstrom), such micropores contributing to the extent of more than 95% of the total area for the most crystalline materials.

2. A composition as claimed in claim 1, characterised in that the tetravalent metal M in formula (I) is chosen from zironium, titanium and tin.

3. A composition as claimed in claim 2, characterised in that said metal is zirconium.

4. A composition as claimed in claim 1, characterised in that all the As in formulas (II) and (III) are other than hydrogen.

5. A composition as claimed in claim 1, characterised by being representable by the following formula:

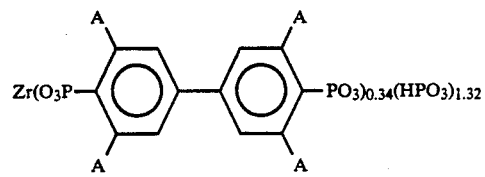

where A is as heretofore defined, the composition having a B.E.T. surface area of about 450 $m^2/g$;

6. A composition as claimed in claim 1, characterised by being representable by the following formula:

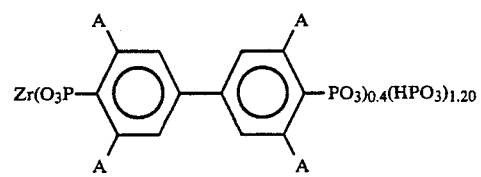

where A is as heretofore defined, said composition having a B.E.T. surface area of about 380 $m^2/g$, micropores of radius less than 20 Å contributing more than 97% of the total area.

7. A process for preparing a composition claimed in any one of claims 1 to 6, characterised by reacting a diphosphonic acid (IIa) or (IIIa):

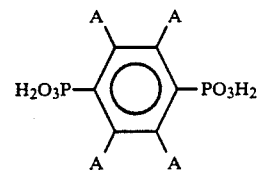

(IIa)

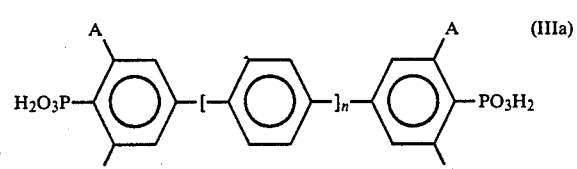

(IIIa)

where A and n have the aforesaid meaning, with phosphorous acid and a soluble salt of a tetravalent metal, operating in a solvent consisting of dimethylsulphoxide/water containing hydrofluoric acid.

8. A process as claimed in claim 7, characterised in that the diphosphonic acid is 4,4,'-bis-phosphono-(3,3',5,5'-tetramethyl)-biphenyl acid.

9. A process as claimed in claim 7, characterised in that the soluble tetravalent metal salt is preferably zirconyl chloride octahydrate $ZrOCL_2 \cdot 8H_2O$.

10. A process as claimed in claim 7, characterised by operating with a molar ratio of diphosphonic acid IIa or IIIa plus phosphorous acid to the tetravalent metal oxychloride of between 1 and 40.

11. A process as claimed in claim 7, characterised in that a concentrated aqueous solution of hydrofluoric acid is used, with a molar ratio of hydrofluoric acid to the tetravalent metal of between 6 and 30.

12. A process as claimed in claim 7, characterised in that the reaction medium is a mixture of dimethylsulphoxide and water.

13. A process as claimed in claim 7, characterised in that the reaction temperature varies between 40° and 130° C. and the reaction time varies between 24 and 240 hours.

14. A process as claimed in claim 13, characterised in that said temperature is of the order of 80° C. and the time about 120 hours.

15. A process as claimed in claim 7, characterised in that the tetravalent metal diphosphonate-phosphate is recovered from the reaction mixture by filtration or centrifuging, is then washed with organic solvent and finally dried.

16. A molecular sieve or a catalyst which is produced by the process of claim 7.

* * * * *